United States Patent [19]
Suzuki

[11] Patent Number: 5,908,857
[45] Date of Patent: Jun. 1, 1999

[54] AGENT FOR THE TREATMENT OF INFECTIONS

[75] Inventor: Fujio Suzuki, 210, Takaya, Shibayama-cho, Sambu-gun, Chiba 289-16, Japan

[73] Assignee: Fujio Suzuki, Chiba, Japan

[21] Appl. No.: 08/704,673

[22] PCT Filed: Mar. 17, 1995

[86] PCT No.: PCT/JP95/00491

§ 371 Date: Sep. 18, 1996

§ 102(e) Date: Sep. 18, 1996

[87] PCT Pub. No.: WO95/25517

PCT Pub. Date: Sep. 28, 1995

[30] Foreign Application Priority Data

Mar. 18, 1994 [JP] Japan .................................. 6-072820
Mar. 18, 1994 [JP] Japan .................................. 6-072821

[51] Int. Cl.⁶ ................................................. A61K 31/40
[52] U.S. Cl. ............................................................ 514/410
[58] Field of Search ............................................. 514/410

[56] References Cited

PUBLICATIONS

Alarcon et al, 1985, 102 CA:39536d.
Abidou et al 1967 67CA:106183k.
C. Atal, et al., "Immunomodulating Agents of Plant Origin. I: Preliminary Screening," Journal of Ethnopharmacology, 18 (1986); pp. 133–141.

V. Merck, et al., "Untersuchungen über den Einsatz Homöopathischer Arzneimittel sur Behandlung akuter Mastitiden beim Rind," Berl Munch Tierarztl Wochenschr, vol. 102, No. 8, 1989; pp. 266–272.

V. Wagner, et al., "Die Beeinflussung der Phagozytosefähigkeit von Granulozyten durch homöopatische Arzneipräparate," Arzneim Forsch/Drug Res, vol. 36, No. 9, 1986; pp. 1421–1425.

R. Pollard, et al., "Effect of Benzoylmesaconine on *Candida albicans* Infection in Mice with Acquired Immunodeficiency Syndrome," U.S. Nat. Lib. of Med., US 31563;95920156, Feb. 2, 1995 (Abstract).

*Primary Examiner*—Russell Travers
*Attorney, Agent, or Firm*—Foley & Lardner

[57] ABSTRACT

The present invention relates an agent for the treatment of infections, which comprises as the active ingredient at least one member selected from the group consisting of aconite-alkaloids, aconite tuber and an extract thereof, gingerol and analogues thereof, and rhizomes of ginger and a substance therefrom.

The agent of the present invention has significant infection-protective and recovery effects and is useful to treat and prevent a variety of infections such as virus infections, fungal infections, opportunistic infections, etc.

6 Claims, 4 Drawing Sheets

NUMBER OF DAYS AFTER INFECTION

NUMBER OF DAYS AFTER INFECTION

AGENT FOR THE TREATMENT OF INFECTIONS

This application is a 371 of PCT/JP95/00491 filed Mar. 17, 1995.

TECHNICAL FIELD

The present invention relates to an agent for the treatment of infections, which is effective against virus infections, fungal infections, etc.

BACKGROUND ART

It is said that the infections have drastically changed in recent years. The classical infections have become latent, while infections that are difficult to treat and occur depending on the resistance of a patient to infections are increasing. Such infections occurring depending on the state of a patient are called opportunistic infections. Typical pathogens for opportunistic infections (herpes simplex virus type I) and their diseases are shown in Table 1. Many of the diseases are serious although they are caused by the same kind of pathogen.

TABLE 1

| first infection | relapse | infection under decreased infection-protective ability |
|---|---|---|
| stomatitis | lip herpes<br>corneal herpes | herpes eczema<br>generalized infection<br>adult encephalitis |

The opportunistic infections refer to the state in which infections have been induced by pathogens of usually little pathogenity because the infection-protective ability of a patient is decreased for some reasons (increased susceptibility to infections). Hence, an agent having a recovery effect of infection-protective ability and an antimicrobial agent effective against pathogens are used to treat the opportunistic infections. In particular, the agent having a recovery effect of infection-protective ability is regarded as indispensable for essential treatment of the opportunistic infections.

However, the opportunistic infections show similar clinical symptoms although many are caused by a plurality of pathogens, and from the clinical symptoms, it is difficult to identify the pathogen, so it is also difficult to select a suitable antimicrobial agent for use in the opportunistic infections. Even if a suitable antimicrobial agent can be selected, substantial treatment of the opportunistic infections would not be achieved until the resistance of the patient is recovered. However, there are not a few cases where the lowered general conditions of the patient permit such an agent having a recovery effect of infection-protective ability to adversely induce a decrease in the infection-protective ability of the patient. At present, there is no agent that can be administered with confidence to treat or prevent the opportunistic infections.

Aconite tuber is tuberous roots of Aconitum carmichaeli of the family Ranunculaceae or other plants of the same genus, and it has been used for a long time as cardiotonic, analgesic, antiphlogistic, etc.

Aconite-alkaloids are aconite tuber-derived alkaloids known to have efficacy as analgesic, antiphlogistic, etc., and typical examples are benzoylmesaconine, benzoylaconine, benzoylhypaconine, 14-anisoylaconine, neoline, ignavine, mesaconine, hypaconine, 16-epi-pyromesaconitine, 16-epi-pyraconitine, 15-α-hydroxyneoline and ajaconine.

Rhizomes of Zingiber officinale Roscoe of the family Zingiberaceae have, for a long time, been used as ginger in medical formulation regarded as peptic, anti-emetic or analgesic, or in other medical formulation. In addition, gingerol as a component of ginger is known to have efficacy as antipyretic, analgesic, etc.

However, aconite tuber or an extract thereof or aconite-alkaloids or derivatives thereof, or ginger, dried ginger or an extract thereof, or gingerol or analogues thereof have never been used to treat infections such as virus infections, fungal infections, opportunistic infections, etc.

DISCLOSURE OF INVENTION

The object of the present invention is to provide an agent for the treatment of infections which has significant recovery effect of infection-protective ability.

The present inventors searched for a pharmaceutical preparation to improve the infection-protective ability of a patient that is decreased for some reasons (increased susceptibility to infections), and the present inventors found that aconite-alkaloids, a plant containing the same or an extract thereof and aconite-alkaloid derivatives, as well as gingerol, a plant containing the same or a substance therefrom and gingerol analogue have inhibitory action on increased susceptibility to infections, and thereby they completed the present invention.

That is, the present invention encompasses:

(1) An agent for the treatment of infections, which comprises as the active ingredient a compound represented by the general formula (I):

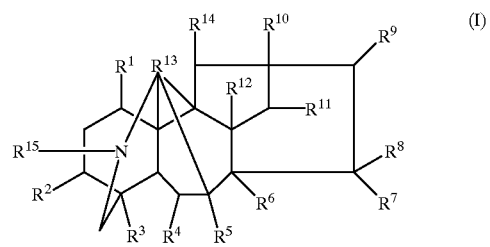

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are the same or different and independently represent a hydrogen atom, hydroxyl group, substituted or unsubstituted $C_1$–$C_7$ alkyl group, substituted or unsubstituted $C_2$–$C_7$ alkenyl group, substituted or unsubstituted $C_2$–$C_7$ alkynyl group, substituted or unsubstituted $C_3$–$C_7$ cycloalkyl group, substituted or unsubstituted $C_4$–$C_7$ cycloalkenyl group, substituted or unsubstituted acyl group, substituted or unsubstituted acyloxy group, substituted or unsubstituted acyloxy-$C_1$–$C_7$ alkyl group, substituted or unsubstituted $C_2$–$C_7$ alkoxycarbonyl group, substituted or unsubstituted $C_2$–$C_7$ alkenyl-oxycarbonyl group, substituted or unsubstituted aryloxycarbonyl group, substituted or unsubstituted $C_1$–$C_7$ alkoxy group, substituted or unsubstituted $C_2$–$C_7$ alkenyloxy group, substituted or unsubstituted $C_2$–$C_7$ alkynyloxy group, substituted or unsubstituted $C_3$–$C_7$ cycloalkyloxy group, substituted or unsubstituted $C_4$–$C_7$ cycloalkenyloxy group, substituted or unsubstituted aryloxy group, substituted or unsubstituted aryl-$C_1$–$C_7$ alkyloxy group, substituted or unsubstituted aryl-$C_2$–$C_7$ alkenyloxy group, substituted or unsubstituted $C_1$–$C_7$ alkoxy-$C_1$–$C_7$ alkyl group or substituted or unsubstituted $C_1$–$C_7$ alkoxy-$C_1$–$C_7$ alkoxy group, or $R^2$ and $R^3$ may together represent an epoxy group, $R^1$ and $R^{14}$ may together represent an epoxy group, and $R^7$ and $R^8$ may together represent an oxo group, or a pharmaceutically acceptable salt thereof.

(2) An agent for the treatment of infections, which comprises as the active ingredient a compound represented by the general formula (II):

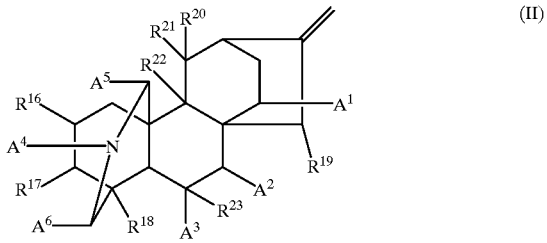

wherein $R^{16}$, $R^{17}$, $R^{18}$, $R^{19}$, $R^{20}$, $R^{21}$, $R^{22}$, $R^{23}$, $A^1$, $A^2$, $A^3$, $A^4$ and $A^5$ are the same or different and independently represent a hydrogen atom, hydroxyl group, substituted or unsubstituted $C_1$–$C_7$ alkyl group, substituted or unsubstituted $C_2$–$C_7$ alkenyl group, substituted or unsubstituted $C_2$–$C_7$ alkynyl group, substituted or unsubstituted $C_3$–$C_7$ cycloalkyl group, substituted or unsubstituted $C_4$–$C_7$ cycloalkenyl group, substituted or unsubstituted acyl group, substituted or unsubstituted acyloxy group, substituted or unsubstituted acyloxy-$C_1$–$C_7$ alkyl group, substituted or unsubstituted $C_2$–$C_7$ alkoxycarbonyl group, substituted or unsubstituted $C_2$–$C_7$ alkenyl-oxycarbonyl group, substituted or unsubstituted aryloxycarbonyl group, substituted or unsubstituted $C_1$–$C_7$ alkoxy group, substituted or unsubstituted $C_2$–$C_7$ alkenyloxy group, substituted or unsubstituted $C_2$–$C_7$ alkynyloxy group, substituted or unsubstituted $C_3$–$C_7$ cycloalkyloxy group, substituted or unsubstituted $C_4$–$C_7$ cycloalkenyloxy group, substituted or unsubstituted aryloxy group, substituted or unsubstituted aryl-$C_1$–$C_7$ alkyloxy group, substituted or unsubstituted aryl-$C_2$–$C_7$ alkenyloxy group, substituted or unsubstituted $C_1$–$C_7$ alkoxy-$C_1$–$C_7$ alkyl group or substituted or unsubstituted $C_1$–$C_7$ alkoxy-$C_1$–$C_7$ alkoxy group, $A^6$ represents a hydrogen atom, and $R^{20}$ and $R^{21}$ and/or $R^{23}$ and $A^3$ may together represent an oxo group, $A^1$ and $A^5$ and/or $A^3$ and $A^4$ may together represent a single bond, $A^2$ and $A^5$ may together represent an epoxy group, and $A^4$ and $A^6$ may together represent an ethyleneoxy group, or a pharmaceutically acceptable salt thereof.

(3) An agent for the treatment of infections, which comprises aconite tuber or an extract thereof as the active ingredient.

(4) An agent for the treatment of infections, which comprises as the active ingredient a compound represented by the general formula (III):

wherein Ar represents a substituted or unsubstituted phenyl group, $R^{24}$ represents a substituted or unsubstituted $C_1$–$C_7$ alkyl group, substituted or unsubstituted $C_2$–$C_7$ alkenyl group, substituted or unsubstituted aryl-$C_1$–$C_7$ alkyl group or substituted or unsubstituted aryl-$C_2$–$C_7$ alkenyl group.

(5) An agent for the treatment of infections, which comprises rhizomes of ginger or a substance therefrom as the active ingredient.

In the present specification, the $C_1$–$C_7$ alkyl group includes for example a methyl group, ethyl group, n-propyl group, isopropyl group, n-butyl group, isobutyl group, sec-butyl group, t-butyl group, pentyl group, hexyl group, and heptyl group. The $C_2$–$C_7$ alkenyl group includes for example a vinyl group, allyl group, propene-2-yl group, but-1-en-4-yl group, and but-2-en-2-yl group. The $C_2$–$C_7$ alkynyl group includes for example an ethynyl group and propargyl group. The $C_3$–$C_7$ cycloalkyl group includes for example a cyclopentyl group and cyclohexyl group. The $C_4$–$C_7$ cycloalkenyl group includes for example a cyclopent-2-enyl group and cyclohex-3-enyl group. The acyl group includes for example an aliphatic acyl group composed of the aforementioned $C_1$–$C_7$ alkyl group, $C_2$–$C_7$ alkenyl group, $C_2$–$C_7$ alkynyl group, $C_3$–$C_7$ cycloalkyl group or $C_4$–$C_7$ cycloalkenyl group; an aromatic acyl group composed of an aryl group such as phenyl group, naphthyl group, pyrrolyl group, pyrazolyl group, imidazolyl group, triazolyl group, tetrazolyl group, furyl group, thienyl group, and pyridyl group, examples being a benzoyl group and anisoyl group; and aryl-$C_1$–$C_7$ alkyl-CO— group and aryl-$C_2$–$C_7$ alkenyl-CO— group composed of the aforementioned aryl group and of the aforementioned $C_1$–$C_7$ alkyl group or $C_2$–$C_7$ alkenyl group. The acyloxy group includes an acyloxy group composed of the aforementioned acyl group, and examples are $C_1$–$C_7$ alkyl-COO—, $C_2$–$C_7$ alkenyl-COO—, $C_2$–$C_7$ alkynyl-COO—, $C_3$–$C_7$ cycloalkyl-COO—, $C_4$–$C_7$ cycloalkenyl- COO—, aryl-COO—, aryl-$C_1$–$C_7$ alkyl-COO—, and aryl-$C_2$–$C_7$ alkenyl-COO—. The acyloxy-$C_1$–$C_7$, alkyl group includes an acyloxyalkyl group composed of the aforementioned acyloxy group and $C_1$–$C_7$ alkyl group, an example is a benzoyloxymethyl group. The $C_2$–$C_7$ alkoxycarbonyl group includes an alkoxycarbonyl group composed of the aforementioned $C_1$–$C_7$ alkyl group. The $C_2$–$C_7$ alkenyl-oxycarbonyl group includes an alkenyloxycarbonyl group composed of the aforementioned $C_2$–$C_7$ alkenyl group. The aryloxycarbonyl group includes an aryloxycarbonyl group composed of the aforementioned aryl group. The $C_1$–$C_7$ alkoxy group includes an alkoxy group composed of the aforementioned $C_1$–$C_7$ alkyl group. The $C_2$–$C_7$ alkenyloxy group includes an alkenylalkoxy group composed of the aforementioned $C_2$–$C_7$ alkenyl group. The $C_2$–$C_7$ alkynyloxy group includes an alkynylalkoxy group composed of the aforementioned $C2$–$C_7$ alkynyl group. The $C_3$–$C_7$ cycloalkyloxy group includes a cycloalkyloxy group composed of the aforementioned $C_3$–$C_7$ cycloalkyl group. The $C_4$–$C_7$ cycloalkenyloxy group includes a cycloalkenyloxy group composed of the aforementioned $C_4$–$C_7$ cycloalkenyl group. The aryloxy group includes an aryloxy group composed of the aforementioned aryl group. The aryl-$C_1$–$C_7$ alkyloxy group includes an arylalkyloxy group composed of the aforementioned aryl group and $C_1$–$C_7$ alkyl group. The aryl-$C_2$–$C_7$ alkenyloxy group includes an arylalkenyloxy group composed of the aforementioned aryl group and $C_2$–$C_7$ alkenyl group. The $C_1$–$C_7$ alkoxy-$C_1$–$C_7$ alkyl group includes an alkoxyalkyl group composed of the aforementioned $C_1$–$C_7$ alkoxy group and $C_1$–$C_7$ alkyl group, and an example is a methoxymethyl group. The $C_1$–$C_7$ alkoxy-$C_1$–$C_7$ alkoxy group includes an alkoxyalkoxy group composed of the aforementioned $C_1$–$C_7$ alkoxy group, and an example is a methoxymethoxy group.

The aforementioned substituent groups may be substituted with a hydroxyl group, halogen atom, nitro group, substituted or unsubstituted amino group, substituted or unsubstituted succinimido group, etc.

As $R^{24}$ in the above formula (III), the aryl-$C_1$–$C_7$ alkyl group includes an aralkyl group composed of the aforementioned aryl group and $C_1$–$C_7$ alkyl group, examples being benzyl group and phenethyl group, and the aryl-$C_2$–$C_7$ alkenyl group includes an arylalkenyl group composed of the aforementioned aryl group and $C_2$–$C7$ alkenyl group, an example being a styryl group.

The active ingredients of the agent of the present invention are not particularly limited insofar as they contain aconite-alkaloids. Examples of active ingredients are aconite-alkaloids such as benzoylmesaconine, benzoylaconine, benzoylhypaconine, 14-anisoyl- aconine, neoline, mesaconine, hypaconine, 16-epi-pyromesaconitine, 16-epi-pyraconitine, 15- α-hydroxyneoline, moticamine, moticoline, lappaconine, Excelsine, delvestidine, N-acetyldelectine, ajacine, anhweidelphinine, methyllycaconitine, avadharidine, septentrionine, andersonine, ajaconine, dihydroajaconine, ignavine, septentriosine, spiradine-C, spiramine-C and spirasine-III, or aconite tuber which is a plant containing them or an extract thereof. A crude drug containing an aconite-alkaloid other than aconite tuber itself or an extract thereof may also be used. Further, a mixed crude drug containing aconite tuber as a constituent crude drug or an extract thereof may also be used.

The aforementioned aconite-alkaloids are known compounds and can be obtained in conventional processes.

The structures of typical aconite-alkaloids are shown below:

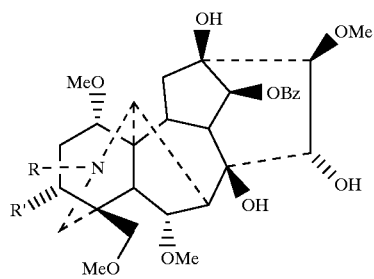

benzoylmesaconine: R = Me, R' = OH
benzoylaconine:    R = Et, R' = OH
benzoylhypaconine: R = Me, R' = H

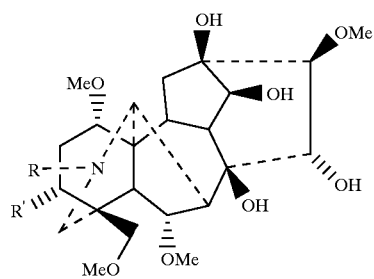

mesaconine: R = Me, R' = OH
hypaconine: R = Me, R' = H

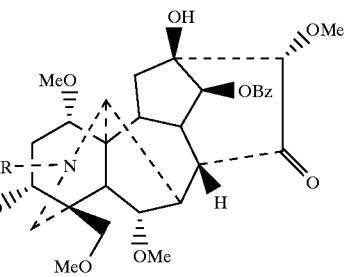

16-epi-pyromesaconitine: R = Me
16-epi-pyraconitine:     R = Et

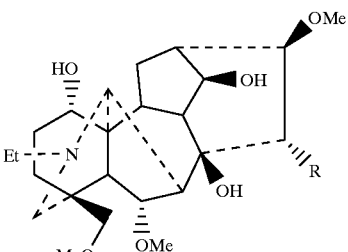

neoline:              R = H
15-α-hydroxyneoline:  R = OH

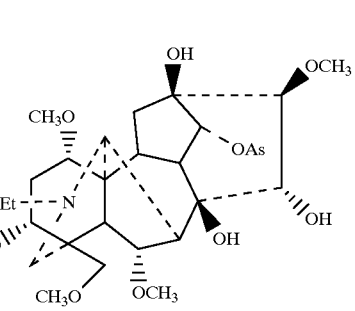

14-anisoylaconine

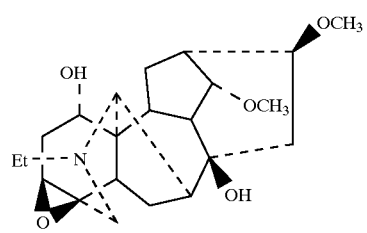

moticamine

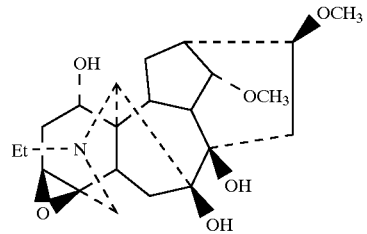

moticoline
E.F. Ametova, M.S. Yunusov
Khim. Prir. Soedin., 466 (1981)

-continued
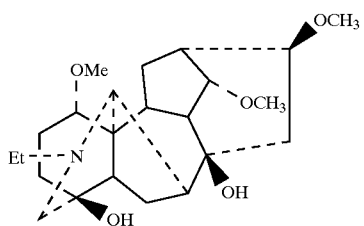
lappaconine
V.A. Telnov, M.S. Yunusov
Khim. Prir. Soedin., 6, 583 (1970)
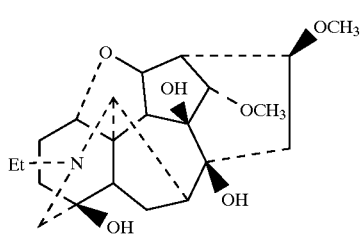
Excelsine
V.A. Telnov, M.S. Yunusov
Khim. Prir. Soedin., 9, 129 (1973)
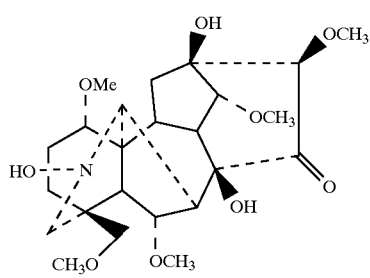
K. Wiesner, F. Bickelhaupt
Experintia 15, 93 (1953)
K. Wiesner, Tetrahedron Letters
No. 3, 11 (1959)
W.A. Jacobs and S.W. Pelletier
J.A.C.S. 76, 161 (1954)
-continued
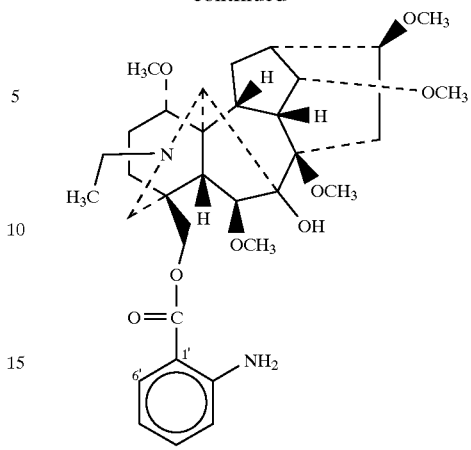
delvestidine
H.K. Desai, et al., Heterocycles, 23, 2483 (1985)
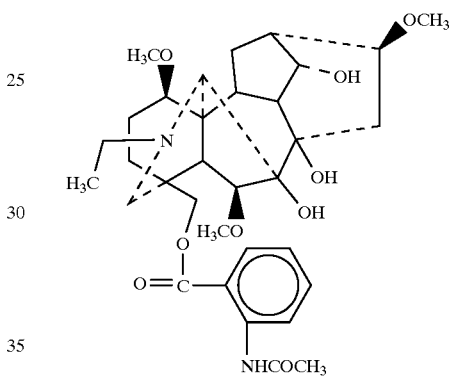
N-acetyldelectine
B.T. Salimov, et al., Khim. Prir. Soedin., 14, 235 (1978)
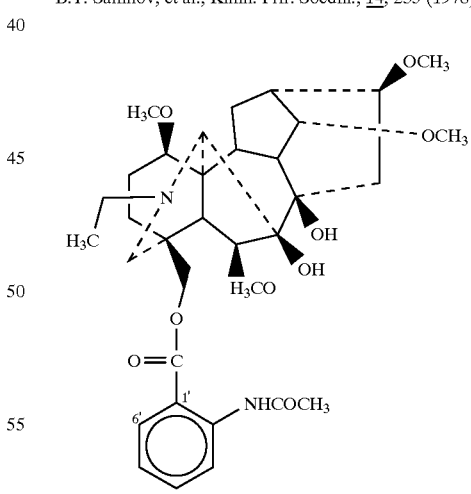
ajacine
S.W. Pelletier, et al., J. Nat. Prod. (Lloydia), 43, 395 (1980)

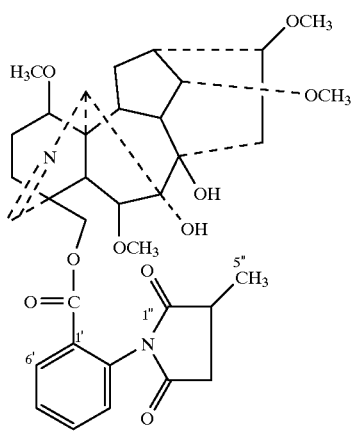
anhweidelphinine
J.S. Jin and M.C. Zhong, Zhongcaoyao, 17, 49 (1986)
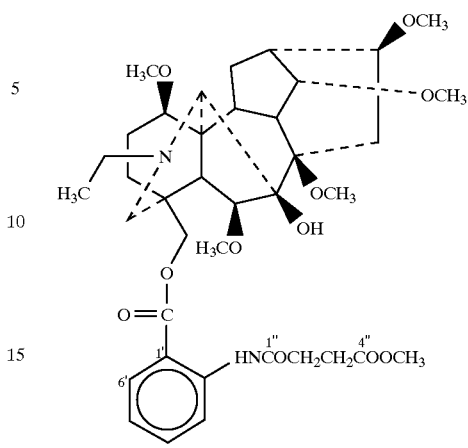
septentrionine
S. W. Pelletier, et al., Hetercycles, 12, 377 (1979)
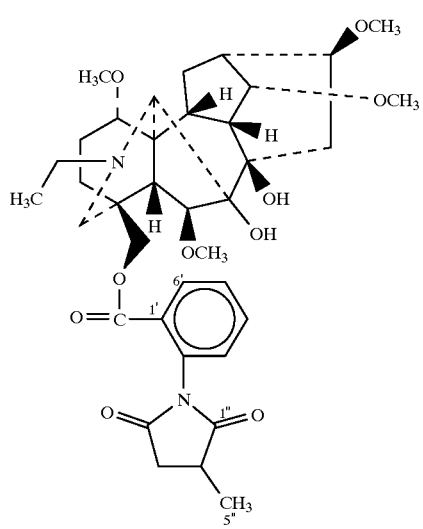
methyllycaconitine
S.W. Pelletier, et al., Heterocycles, 27, 2387 (1988)
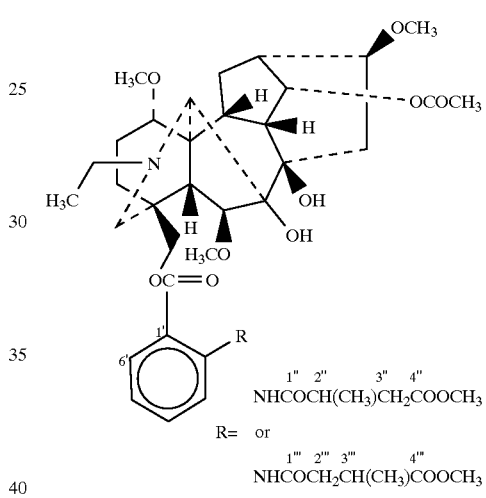
andersonine
S. W. Pelletier, et al., Heterocycles, 27, 2387 (1988)
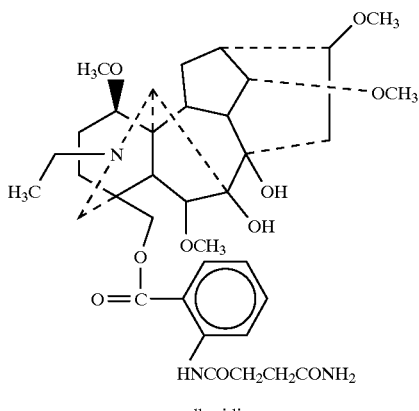
avadharidine
M. Shamma, et al., J. Nat. Prod. (Lloydia), 42, 615 (1979)
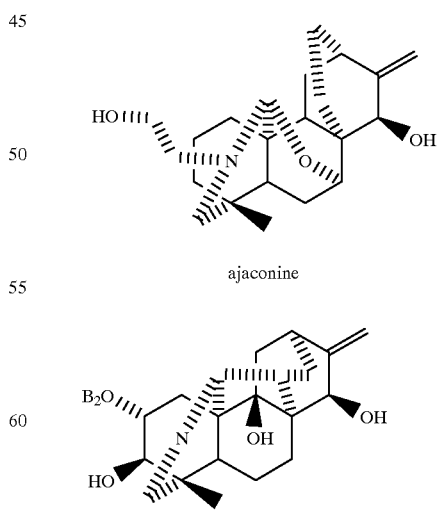
ajaconine
ignavine

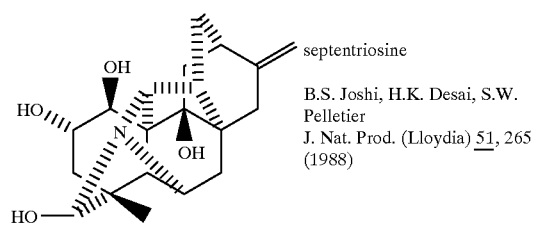
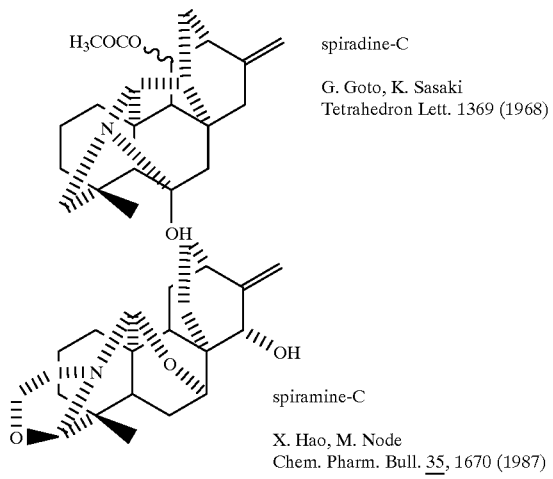
It is further possible to make use of esterified, etherified or acylated derivatives prepared for example in the following manner:
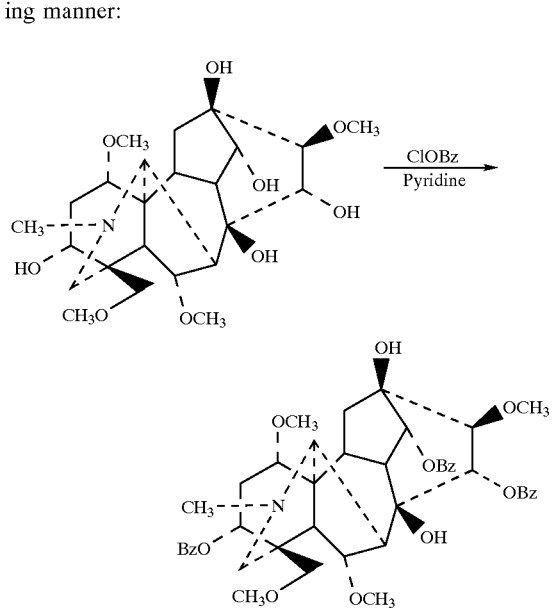
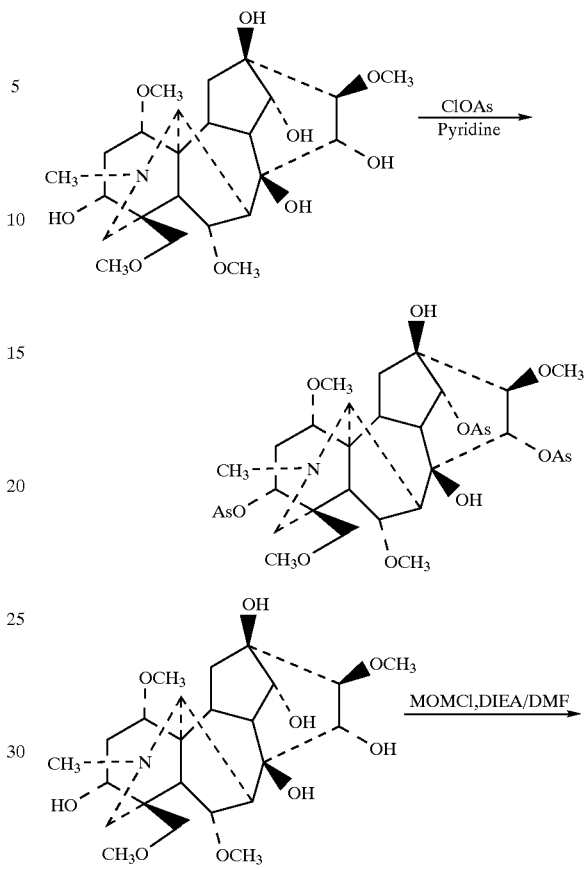

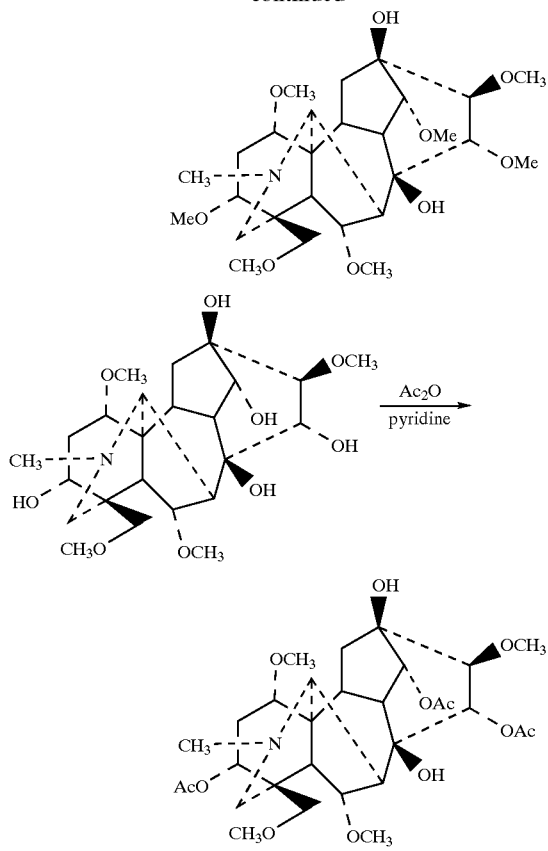

wherein Bz stands for benzoyl group, As for anisoyl group, MOM for methoxymethyl group, DIEA for N,N-diisopropylethylamine, and Ac for acetyl group.

An extract from the above crude drug includes those extracted with a variety of aqueous solvents, preferably water. For example, the extract can be obtained by extracting the crude drug with a 10- to 20- fold volume of hot water and filtering the extract. If necessary, the extract may be dried for use as dried powder.

As the active ingredients of the present agent, rhizomes of ginger and a substance therefrom may be used in any form such as ginger, dried ginger or an extract thereof. A mixed crude drug containing ginger or dried ginger as a constituent crude drug or an extract thereof may also be used.

The above extract includes those extracted with a variety of aqueous solvents, preferably water. For example, the extract can be obtained by extracting the crude drug with a 10- to 20-fold volume of hot water and filtering the extract. If necessary, the extract can be dried for use as dried powder.

The preparation of an aconite tuber extract as one of the active ingredients of the present agent is illustrated by reference to the following specific examples.

SPECIFIC EXAMPLE 1

400 ml of distilled water was added to 20 g of aconite tuber and boiled to evaporate half the volume. The extract was filtered and lyophilized to give 5.5 g of dried extract.

SPECIFIC EXAMPLE 2

After addition of 4 L of purified water, 200 g of aconite tuber was extracted by heating for 1 hour at 100° C. The extract was centrifuged to separate the residue. The supernatant was filtered through a 0.3 μm membrane filter (Toyo Roshi Co., Ltd.) to remove bacteria. The transparent filtrate was ultrafiltrated at a pressure of 3 kg/cm² through Diafilter G-10T™ of 152 mm in diameter (Bioengineering Co., Ltd.; a fractionation molecular weight of 10,000) attached to the bottom of a 2.0 L vessel while purified water was added as the solution became concentrated in the vessel. The ultrafiltrate was thus obtained.

As the active ingredients of the present agent, aconite-alkaloids such as benzoylmesaconine, benzoylaconine, benzoylhypaconine, 14-anisoylaconine, neoline, mesaconine, hypaconine, 16-epi-pyromesaconitine, 16-epi-pyraconitine, $^{15}$-a-hydroxyneoline, moticamine, moticoline, lappaconine, Excelsine, ajaconine, dihydroajaconine, ignavine, septentriosine, spiradine-C, spiramine-C and spirasine-III can be obtained by suitable extraction of aconite tuber (see for example Yakugaku Zasshi, 104 (8), 858–866 (1984)).

The preparation of an extract from dried ginger as an active ingredient of the present agent is illustrated by reference to the following specific examples.

SPECIFIC EXAMPLE 3

400 ml of distilled water was added to 20 g of dried ginger and boiled to evaporate half the volume. The extract was filtered and lyophilized to give 3.5 g of dried extract.

SPECIFIC EXAMPLE 4

After addition of 4 L of purified water, 200 g of dried ginger was extracted by heating for 1 hour at 100° C. The extract was centrifuged to separate the residue. The supernatant was filtered through a 0.3 μm membrane filter (Toyo Roshi Co., Ltd.) to remove bacteria. The transparent filtrate was ultrafiltrated at a pressure of 3 kg/cm² through Diafilter G-10T™ of 152 mm in diameter (Bioengineering Co., Ltd.; a fractionation molecular weight of 10,000) attached to the bottom of a 2.0 L vessel while purified water was added as the solution became concentrated in the vessel. The ultrafiltrate was thus obtained.

As the active ingredient of the present agent, gingerol can be obtained by suitable extraction of ginger or dried ginger (see for example Australian Journal of Chemistry, 22, 1033 (1969)).

The infection-therapeutic action of the active ingredients of the present agent is described by reference to the following experimental examples.

EXPERIMENTAL EXAMPLE 1

The action of the active ingredients of the present agent was examined in terms of suppressor cell activities induced in a model of increased susceptibility to infections (thermally injured mice) previously reported in FASEB Journal, 6, 1981 (1992) by the present inventors.

(1) Model of increased susceptibility to infection (thermally injured mice)

8-week-old BALB/c male mice were anesthetized by intraperioneally administrating 0.8 mg/20 g of pentobarbital. The hair between the thighs and armpits of the mice was removed with a pair of hair clippers, and third degree burns (about 30% of body area on 20 g mouse) were generated on the mice by attaching the bared skin to an asbestos wire gauze (2×3 cm) previously heated by a gas burner. Immediately after burns were generated, the mice were intraperioneally given 3 ml of physiological saline as the model of increased susceptibility to infections (thermally injured mice). As normal mice, other mice were treated in the same manner except that the operation of generating burns was not carried out.

(2) Determination of survival rate

One day after burns were generated, the mice were infected intraperioneally with $3 \times 10^3$ PFU/kg of herpes simplex virus type I. One day before the infection, 1 day and 4 days after the infection, the thermally injured mice were orally given each of the active ingredients of the present agent (4 mg/kg of aconite tuber extract or 1 $\mu$ g/kg of aconite-alkaloid) through a stomach probe. Twenty-five days after the infection, their survival rate was determined by comparison with those of the control groups, i.e. the thermally injured mice infected with herpes simplex virus type I and the normal mice infected with the same virus.

TABLE 2

| active ingredient | average survival days | survival rate (%) |
|---|---|---|
| control group of infected thermally injured mice | 11.8 | 0 |
| control group of infected normal mice | >24.4 | 90 |
| aconite tuber extract obtained in Specific Example 1 | >22.8 | 85 |
| benzoylmesaconine | >21.5 | 85 |
| benzoylaconine | >22.5 | 80 |
| benzoylhypaconine | >22.4 | 80 |
| 14-anisoylaconine | >22.5 | 80 |
| neoline | >22.3 | 80 |
| ignavine | >21.9 | 75 |
| mesaconine | >23.1 | 85 |
| hypaconine | >23.1 | 85 |
| 16-epi-pyromesaconitine | >22.4 | 80 |
| 16-epi-pyraconitine | >21.2 | 70 |
| 15-α-hydroxyneoline | >20.9 | 70 |
| ajaconine | >22.3 | 80 |

(3) Measurement of contrasuppressor cell activities

Contrasuppressor cell activities, i.e. cells activities suppressing the suppressor cell activities induced in thermally injured mice were determined in mixed lymphocyte tumor cell reaction (MLTR) by mixing and incubating the following cells for 5 days in a 96-wells round-bottom microplate. Reaction cells: Spleen mononuclear cells (referred to hereinafter as SMNCs) ($5.0 \times 10^4$ cells/well) obtained from normal BALB/c mice. Stimulator cells: EL-4 tumor cells ($5.0 \times 10^4$ cells/well). Suppressor cells: SMNCs ($2.5 \times 10^5$ cells/well) obtained from the model of increased susceptibility to infections. Contrasuppressor cells: SMNCs ($2.5 \times 10^5$ cells/well) obtained from a model (BALB/c mice) of increased susceptibility to infections, previously given an active ingredient of the present agent (4 mg/kg of aconite tuber extract, or 1 $\mu$ g/kg of aconite-alkaloid) twice every third day.

Before incubation, the cells except for the reaction cells were treated with 40 $\mu$ g/ml of mitomycin C solution at 37° C. for 30 minutes. Twenty-four hours before the conclusion of 3-days incubation, 0.5 $\mu$ Ci/well of $^3$H-thymidine was added to the well, and the amount of $^3$H-thymidine incorporated into the reaction cells was determined in a liquid scintillation counter to evaluate the contrasuppressor cell activities induced against the suppressor cell activities by administration of the active ingredient of the present agent.

The results are shown in Tables 3 and 4.

TABLE 3

| active ingredient | incorporation of $^3$H-thymidine (CPM ± SE) |
|---|---|
| incubation of reaction cells and stimulator cells (normal model) | 12413 ± 1438 |
| incubation of reaction cells, stimulator cells and suppressor cells (model of increased susceptibility to infection) | 2650 ± 70 |
| aconite tuber extract obtained in Specific Example 1 | 15888 ± 1775 |

TABLE 4

| active ingredient | incorporation of $^3$H-thymidine (CPM ± SE) |
|---|---|
| incubation of reaction cells and stimulator cell (normal model) | 12413 ± 1438 |
| incubation of reaction cells stimulator cells and suppressor cells (model of increased susceptibility to infection) | 2650 ± 70 |
| benzoylmesaconine | 14754 ± 1832 |
| benzoylaconine | 16140 ± 1738 |
| benzoylhypaconine | 21319 ± 903 |
| 14-anisoylaconine | 12720 ± 1578 |
| neoline | 13744 ± 526 |
| ignavine | 12831 ± 2255 |
| mesaconine | 15791 ± 2778 |
| hypaconine | 14111 ± 2232 |
| 16-epi-pyromesaconitine | 16891 ± 2232 |
| 16-epi-pyraconitine | 15654 ± 1209 |
| 15-α-hydroxyneoline | 14498 ± 1960 |
| ajaconine | 17655 ± 1879 |

EXPERIMENTAL EXAMPLE 2

In this example, 7-week-old BALB/c mice were infected intraperioneally with a lethal dose ($3 \times 10^5$ PFU/kg) of herpes simplex virus type I. Two days before the infection, 1 day and 4 days after the infection, the active ingredient of the present agent (10$\mu$ g/kg) or physiological saline (control) was orally administered through a stomach probe into the mice. Twenty-five days after the infection, their survival rate was determined to evaluate the action of the active ingredient. In this experiment, the experimental mice were given the active ingredient of the present agent before and after infection with the virus to evaluate its action mainly on the prevention and treatment of the virus infection.

The result of the extract from dried ginger obtained in Specific Example 3 is shown in Table 5. The result of gingerol is shown in Table 6.

TABLE 5

| administered agent | average survival days | survival rate (%) |
|---|---|---|
| physiological saline (control) | 12.4 | 0 |
| extract of dry ginger obtained in Specific Example 3 | >23.1 | 70 |

TABLE 6

| administered agent | average survival days | survival rate (%) |
| --- | --- | --- |
| physiological saline (control) | 8.5 | 0 |
| gingerol | >24.4 | 90 |

EXPERIMENTAL EXAMPLE 3

Mice as opportunistic infection model inoculated intraperioneally with 0.1 ml/mouse of a culture supernatant of AIDS virus (LP-BM5 virus) infected SC-1 cells were orally given benzoylmesaconine or physiological saline. Then, the mice were observed for 150 days to determine their survival rate. The results are shown in Table 7.

TABLE 7

| administered agent | number of mice | survival rate (%) |
| --- | --- | --- |
| physiological saline (0.2 ml/mouse) | 10 | 0 |
| benzoylmesaconine (1 μg/kg) | 10 | 80 |

The contrasuppressor cell activities induced against suppressor cell activities by administration of benzoylmesaconine was evaluated in the same manner as in "(3) Measurement of contrasuppressor cell activities" in Experimental Example 1. As suppressor cells, spleen mononuclear cells were prepared from mice 110 days after infection with LP-BM5 virus. The results are shown in Table 8.

TABLE 8

| administered agent | incorporation of $^3$H-thymidine (CPM ± SE) | suppressing rate* (%) |
| --- | --- | --- |
| physiological saline (0.2 ml/mouse) | 1,730 ± 289 | 81 |
| benzoylmesaconine (1 μg/kg) | 8,826 ± 535 | 4 |

*Suppressing rate = [(incorporation in normal model minus incorporation in contrasuppressor cells)/(incorporation in normal model minus incorporation in model of increased susceptibility to infection)] × 100

EXPERIMENTAL EXAMPLE 4

Mice as opportunistic infection model 80 days after intraperioneal infection with 0.1 ml/mouse of a culture supernatant of AIDS virus (LP-BM5 virus) infected SC-1 cells were inoculated intraperioneally with $1 \times 10^3$ PFU/kg of herpes simplex virus type I (HSV). Then, the mice were orally given benzoylmesaconine or physiological saline daily for 30 days beginning 60 days after the infection with the AIDS virus and observed daily to determine their survival rate. The results are shown in FIG. 1.

EXPERIMENTAL EXAMPLE 5

Mice as opportunistic infection model 80 days after intraperioneal infection with 0.1 ml/mouse of a culture supernatant of AIDS virus (LP-BM5 virus) infected SC-1 cells were inoculated intravenously with $3 \times 10^5$ cells/mouse of Candida albicans. Then, the mice were orally given benzoylmesaconine or physiological saline daily for 30 days beginning 60 days after the infection with the AIDS virus and observed daily to determine their survival rate. The results are shown in FIG. 2.

EXPERIMENTAL EXAMPLE 6

Mice as opportunistic infection model inoculated intraperioneally with 0.1 ml/mouse of a culture supernatant of AIDS virus (LP-BM5 virus) infected SC-1 cells were inoculated intravenously with $3 \times 10^5$ cells/mouse of Candida albicans, and the effect of benzoylmesaconine by oral administration was examined. The mice were slaughtered 2, 7 and 14 days after inoculation with Candida albicans, and the number of alive bacteria in the kidney was determined by the colony counting method. The results are shown in FIG. 3.

EXPERIMENTAL EXAMPLE 7

Thermally injured mice were infected intravenously with $2.5 \times 10^3$ PFU/mouse of cytomegalovirus (CMV), then given orally benzoylmesaconine (10 μ g/kg/day) or physiological saline (0.2 ml/mouse/day), and observed for 25 days after the infection. The opportunistic infection of the thermally injured mice to CMV was efficiently protected by administration of benzoylmesaconine. The results are shown in Table 9.

TABLE 9

| administered agent | number of mice | average survival days | rate (%) survival rate (%) |
| --- | --- | --- | --- |
| physiological saline (control) | 10 | 12.4 | 0 |
| benzoylmesaconine | 10 | >22.1 | 100 |

EXPERIMENTAL EXAMPLE 8

SCID mice inoculated with $5 \times 10^6$ cells/mouse of peripheral lymphocytes (suppressor cells) from patients with burns were infected with $2.5 \times 10^3$ PFU/mouse of CMV. Then, the mice were orally given benzoylmesaconine (10 μ g/kg/day) or physiological saline (0.2 ml/mouse/day). As shown in Table 10, the results indicated the protective effect of benzoylmesaconine on CMV.

TABLE 10

| administered agent | number of mice | survival rate (%) |
| --- | --- | --- |
| physiological saline (control) | 10 | 0 |
| benzoylmesaconine | 10 | 100 |

EXPERIMENTAL EXAMPLE 9

Mice 1 day after burns generated as opportunistic infection model were infected with $2 \times 10^4$ cells/mouse of Candida albicans and then given intraperioneally benzoylmesaconine (1 μ g/kg) or physiological saline (0.2 ml/mouse). As a result, the resistance of the thermally injured mice to the fungal infection was completely recovered (see FIG. 4).

EXPERIMENTAL EXAMPLE 10

Spleen mononuclear cells, total T cells, CD4$^+$ T cells and CD8$^+$ T cells were prepared from spleens of mice as opportunistic infection model 80 days after infection with LP-BM5 virus. The reaction cells, stimulator cells and suspected suppressor cells were used in the ratio of 1:1:5, and the mixed lymphocyte tumor cell reaction (MLTR) was carried out in the same manner as in "(3) Measurement of contrasuppressor cell activities" in Experimental Example 1.

As MLTR control, 5×10⁴ cells/well of the reaction cells were incubated with only the stimulator cells. The results are shown in Table 11.

TABLE 11

| cells used in MLTR | incorporation of $^3$H-thymidine (CPM ± SE) | suppressing rate* (%) |
|---|---|---|
| MLTR control | 15,330 ± 726 | — |
| spleen mononuclear cells | 3,066 ± 122 | 80 |
| total T cells | 2,759 ± 105 | 82 |
| CD4⁺ T cells | 14,870 ± 873 | 3 |
| CD8⁺ T cells | 2,300 ± 118 | 85 |

*Suppressing rate = [(incorporation in MLTR control minus incorporation in suppressor cells)/(incorporation in MLTR control)] × 100

In Table 11, the cells responsible for suppressor activities are suggested to be CD8⁺ T cells.

When normal CD8$^{30}$ T cells and CD8⁺ suppressor T cells were incubated for 24 to 72 hours under $CO_2$ in the absence of stimulation, interleukin 4 and interleukin 10 activities were found in the culture.

Furthermore, thermally injured mice became resistant to Candida albicans infection by replacement of their CD8⁺ suppressor T cells by normal CD8⁺ T cells. On the other hand, the susceptibility of normal mice to infections was increased by introduction of CD8⁺ suppressor T cells from thermally injured mice, and their resistance to infections was recovered by removal of the introduced CD8⁺ suppressor T cells with antibodies and subsequent reconstitution with normal T cells. These results indicate that CD8⁺ suppressor T cells act an important role in fungal infections as well.

From the foregoing results, it is evident that the active ingredients of the present agent have a significant effect on the inhibition of increased susceptibility to infections as well as therapeutic effects on infections such as virus infections, fungal infections, etc. Hence, the present agent is useful to treat and prevent infections such as virus infections, fungal infections, opportunistic infections, etc.

An active ingredient of the present agent, i.e. aconite tuber or an extract thereof can be used with confidence because it has a long history in itself or as a constituent crude drug of a Chinese herbal remedy and its safety was confirmed. This is also evidenced by the fact that every mouse and rat survived after oral administration of 10 g of aconite tuber. The acute toxicities [$LD_{50}$ (mg/kg)] of aconite- alkaloids such as benzoylmesaconine, benzoylaconine, benzoylhypaconine, 14-anisoylaconine, neoline, ignavine, mesaconine, hypaconine, 16-epi-pyromesaconitine, 16-epi-pyraconitine, $^{15}$-α-hydroxyneoline and ajaconine differ from one another but generally range from about 20 to 500 mg/kg.

Another active ingredient of the present agent, i.e. ginger, dried ginger or an extract thereof can also be used with confidence because it has a long history in itself or as a constituent crude drug of a Chinese herbal remedy and its safety was confirmed as well. For example, the acute toxicity [$LD_{50}$ (mg/kg)] of an extract of dried ginger (extracted with water) was reported to be 33500 in terms of crude drug toxicity (Shoyakugaku Zasshi, 37 (1), 37–83 (1983)). The acute toxicity of gingerol [$LD_{50}$ (mg/kg)] is generally about 250 mg/kg (J. Pharm. Dyu.7, 836–848 (1984)).

Hereinafter, the agent of the present invention will be further described by reference to pharmaceutical manufacturing and dosage.

The present agent can be manufactured into pharmaceuticals by combining the aforementioned active ingredient with suitable pharmaceutical carriers. The agent can be administered in any form. For example, it can be administered orally in the form of tablet, capsule, granule, fine granule, powder, etc., or parenterally in the form of suppository, injection, external preparation, etc.

In order to achieve the desired effect, the dose of the active ingredient depends on the weight and age of a patient and the degree of disease. The dose of the active ingredient per day, administered at intervals into an adult, is preferably about 0.5 to 2 g for aconite tuber, about 50 $\mu$ g to 5 mg for aconite-alkaloids, about 0.5 to 9 g for ginger or dried ginger, and about 50$\mu$ g to 100 mg for gingerol.

A pharmaceutical preparation to be orally administered is manufactured in a usual manner using starch, lactose, sucrose, mannitol, carboxymethylcellulose, corn starch, inorganic salts, etc.

If necessary, this type of preparation can make use of binders, disintegrators, surfactants, lubricants, enhancers for the fluidity, flavoring agents, colorants, perfumes, etc. Examples are as follows: [Binders]

Starch, dextrin, powdered acacia, gelatin, hydroxypropyl starch, methylcellulose, carboxymethylcellulose sodium, hydroxypropyl-cellulose, microcrystalline cellulose, ethylcellulose, polyvinylpyrrolidone, Macrogol. [Disintegrators]

Starch, hydroxypropyl starch, carboxymethylcellulose sodium, carboxymethylcellulose calcium, carboxymethylcellulose, low-substituted hydroxypropylcellulose. [Surfactants]

Sodium lauryl sulfate, soybean lecithin, sucrose esters of fatty acid, polysorbate 80. [Lubricants]

Talc, waxes, hydrogenated vegetable oils, sucrose esters of fatty acid, magnesium stearate, calcium stearate, aluminum stearate, poly(ethyleneglycol). [Enhancers for the fluidity]

Light anhydrous silicic acid, dried aluminum hydroxide gel, synthetic aluminum silicate, magnesium silicate.

The present agent can also be administered in the form of suspension, emulsion, syrup or elixir, and it may contain corrigents and colorants.

Pharmaceutical preparations parenterally administrated, for example external preparations such as ointment, lotion, liniment, etc., are manufactured in a usual manner generally using carriers (base materials) such as liquid paraffin, Iso-Par, vaseline, silicone oil, aliphatic higher alcohols (palmityl alcohol, oleyl alcohol), higher aliphatic acids (myristic acid, stearic acid), esters of fatty acid (microcrystalline wax, isopropyl myristate, etc.), lanolin, plastibase (a mixture of liquid paraffin and polyethylene), poly(ethyleneglycol), water, etc. Where required, it is possible to add emulsifiers (fatty acid monoglyceride, sorbitan ester of fatty acid, polyoxyethylene lauryl ether, etc.), wetting agents (glycerin, propylene glycol, sorbitol, etc.), antiseptics (methyl or propyl paraoxybenzoate etc.), antioxidants (BHA etc.), pH adjusting agent (citric acid etc.), suspending agents (CMC etc.) and other pharmaceuticals (itching-preventive agent, analgesic, etc.). Preparations to be percutaneously absorbed fall into the aforementioned preparations.

For preparation of injections, use can be made of diluent that is generally distilled water for injection, physiological saline, an aqueous glucose solution, vegetable oils for injection, sesame oil, peanut oil, soybean oil, corn oil, poly(propyleneglycol), poly(ethyleneglycol), etc. If necessary, disinfectants, antiseptics and stabilizers may also be added. For the sake of stability, an injection preparation may be manufactured as a lyophilized sample etc. in vials so that a liquid preparation is reconstituted just before use. If required, isotonic agents, stabilizers, disinfectants and soothing agents may further be added.

In order to achieve the desired effect, the content of the active ingredient of the present agent in the preparation depends on the dosage form, the age of the patient and the degree of disease. The dose for external preparation is generally 0.01 to 5, preferably 0.1 to 0.5 $\mu$g per gram of base material.

BRIEF DESCRIPTION OF DRAWINGS

In FIG. 1, the symbol ○ represents a group given 1 $\mu$ g/kg/day of benzoylmesaconine, the symbol △ represents a group given 0.1 $\mu$ g/kg/day of benzoylmesaconine, and the symbol ● represents a group given physiological saline.

In FIG. 2, the symbol □ represents a group given 1 $\mu$ g/kg/day of benzoylmesaconine, the symbol ■ represents a group given 10$\mu$ g/kg/day of benzoylmesaconine, and the symbol ● represents a group given physiological saline.

In FIG. 3, the symbol ▨ represents a group given 1 $\mu$ g/kg/day of benzoylmesaconine, and the symbol ■ represents a group not given benzoylmesaconine.

In FIG. 4, the symbol ● represents a group given benzoylmesaconine, and the symbol ○ represents a group given physiological saline.

BEST MODE FOR CARRYING OUT THE INVENTION

Figure 1:
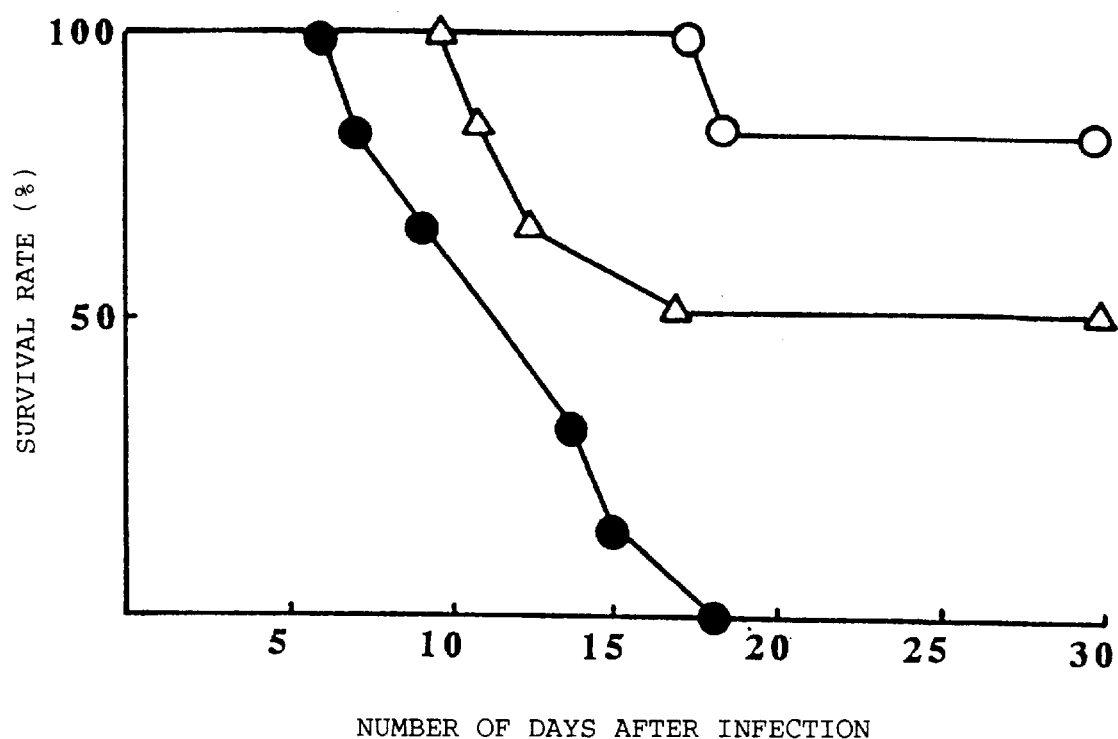
FIG. 1 shows the effect of benzoylmesaconine on the survival rate of HSV-infected mice.
Figure 2:
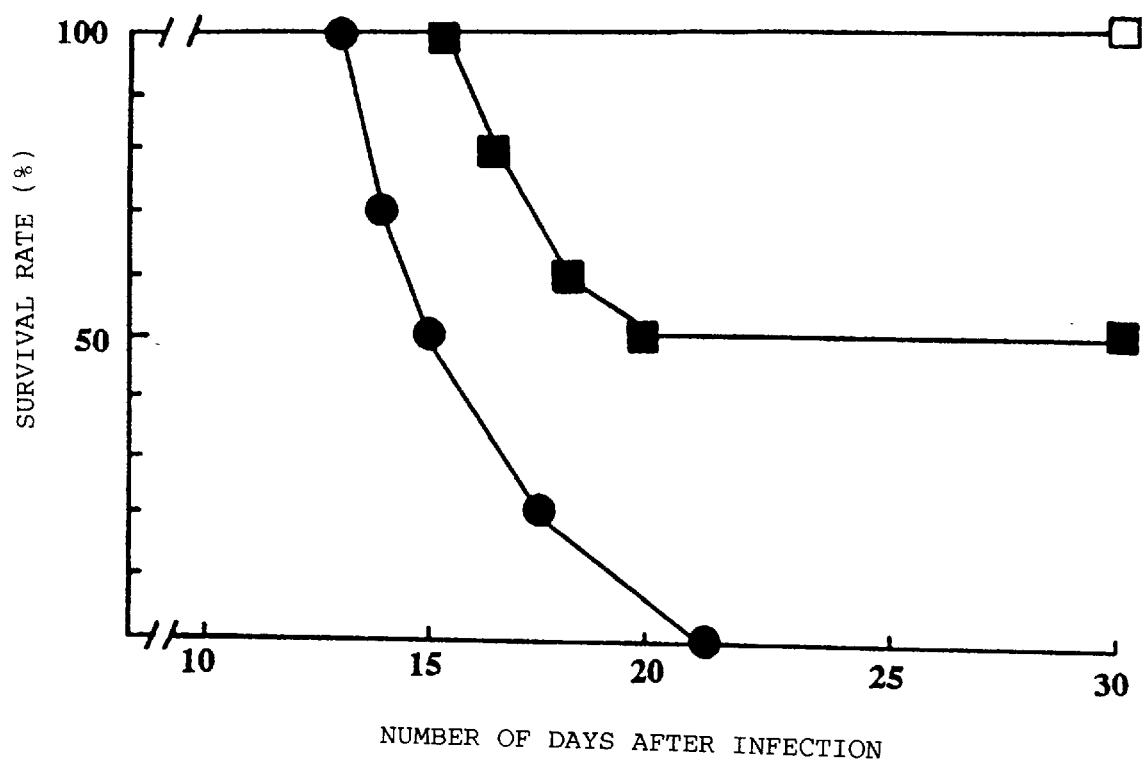
FIG. 2 shows the effect of benzoylmesaconine on the survival rate of Candida albicans-infected mice.
Figure 3:
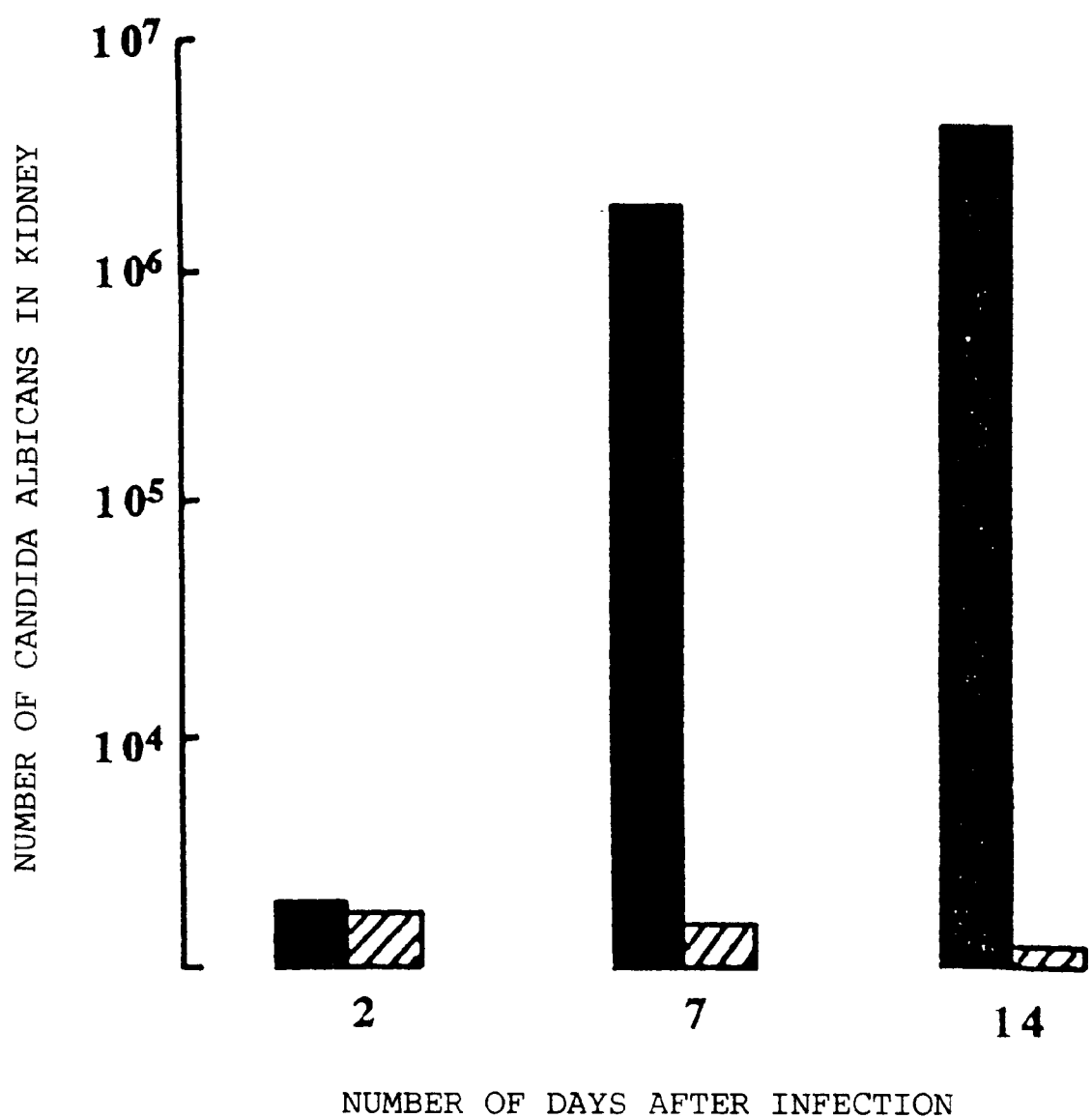
FIG. 3 shows the effect of benzoylmesaconine on the propagation of Candida albicans in the kidney.
Figure 4:
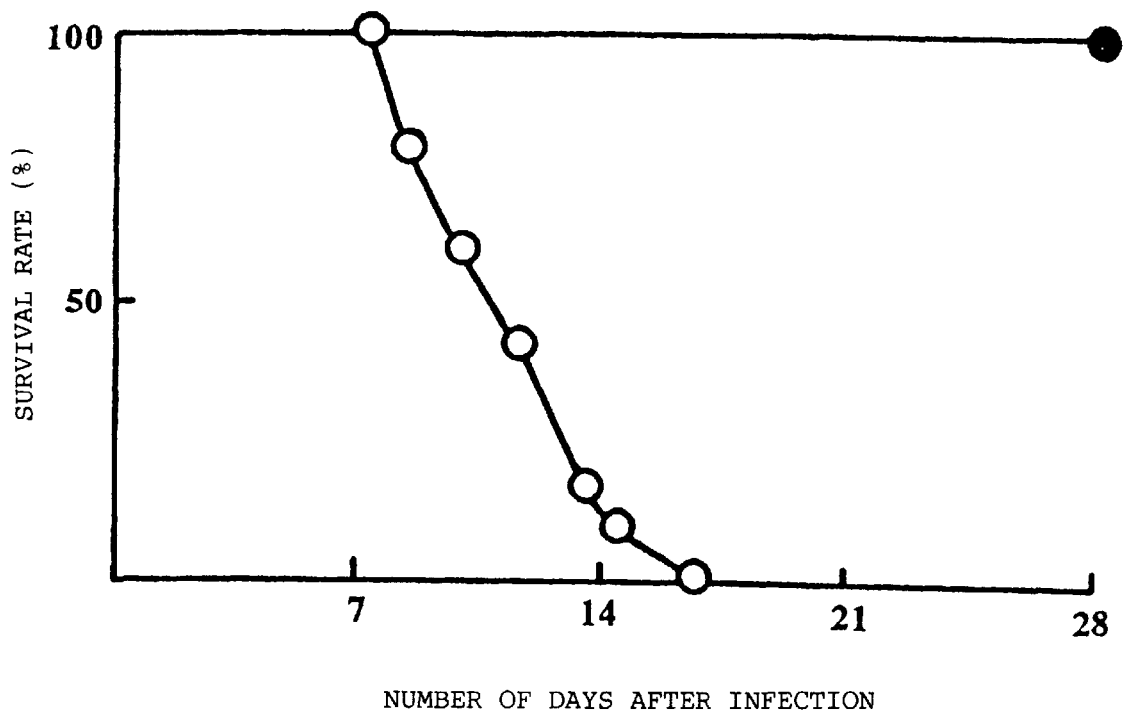
FIG. 4 shows the effect of benzoylmesaconine on the survival rate of thermally injured mice infected with Candida albicans.

The pharmaceutical manufacturing of the agent of the present invention is described in more detail by reference to the following examples, which however are not intended to limit the present invention.

EXAMPLE 1

| | |
|---|---|
| (1) Corn starch | 21 g |
| (2) Microcrystalline cellulose | 10 g |
| (3) Carboxymethylcellulose calcium | 7 g |
| (4) Light anhydrous silicic acid | 1 g |
| (5) Magnesium stearate | 1 g |
| (6) Dried extract of aconite tuber obtained in Specific Example 1 | 160 g |
| total | 200 g |

The ingredients (1) to (6) were uniformly mixed and compression-moulded in a compression machine to give tablets (200 mg/tablet).

One tablet contains 160 mg of the dried extract of aconite tuber obtained in Specific Example 1, and 20–80 tablets are administered daily into an adult at suitable intervals.

EXAMPLE 2

| | |
|---|---|
| (1) Corn starch | 188 g |
| (2) Magnesium stearate | 2 g |
| (3) Carboxymethylcellulose calcium | 8 g |
| (4) Light anhydrous silicic acid | 1 g |
| (5) Benzoylmesaconine | 1 g |
| total | 200 g |

The ingredients (1) to (5) were uniformly mixed, compression-moulded in a compression machine, ground in a crusher and screened to give granules.

One gram of the granules contains 5 mg of benzoylmesaconine and 0.5–5 g of the granules is administered daily into an adult at suitable intervals.

EXAMPLE 3

| | |
|---|---|
| (1) Corn starch | 198.5 g |
| (2) Light anhydrous silicic acid | 1 g |
| (3) 14-anisoylaconine | 0.5 g |
| total | 200 g |

The ingredients (1) to (3) were uniformly mixed and 200 mg was introduced into No. 2 capsule.

One capsule contains 0.5 mg of 14-anisoylaconine and 1–4 capsules are administered daily into an adult at suitable intervals.

EXAMPLE 4

300 g of alanine (pyrogen-free) was added to 20 L of a solution containing the aconite tuber extract obtained in Specific Example 2, and it was dissolved and lyophilized. The lyophilized sample was introduced into 900 vials to give an injection. This injection was of permeability sufficient to pass the pyrogen test in accordance with the Japanese Pharmacopoeia.

EXAMPLE 5

| | |
|---|---|
| (1) 16-epi-pyromesaconitine | 0.05 g |
| (2) Isopropyl myristate | 5 g |
| (3) Plastibase | 94.95 g |

The ingredients (1) and (2) were mixed and added gradually to the ingredient (3) with stirring. The mixture was homogenized to give an oily ointment.

EXAMPLE 6

| | |
|---|---|
| (1) 15-α-hydroxyneoline | 0.05 g |
| (2) Isopropyl myristate | 5.95 g |
| (3) Isopropyl myristate | 10 g |
| (4) Vaseline | 66 g |
| (5) Liquid paraffin | 5 g |
| (6) Microcrystalline wax | 13 g |

The ingredients (3) to (6) were molten by heating, and a mixture of (1) and (2) was added thereto at 45 to 50° C. It was homogenized with stirring until it was solidified to form an oily ointment.

EXAMPLE 7

| | |
|---|---|
| (1) Ajaconine | 0.05 g |
| (2) Poly(ethyleneglycol) (400) | 11.95 g |
| (3) Poly(ethyleneglycol) (400) | 12 g |
| (4) Poly(ethyleneglycol) (4000) | 76 g |

The ingredients (3) and (4) were molten at 70° C., and a mixture of (1) and (2) was added thereto at 50° C. It was homogenized with stirring until it was solidified to form a hydrophilic ointment. Carbol 934 ™ can further be mixed with the hydrophilic ointment.

EXAMPLE 8

| | |
|---|---|
| (1) Corn starch | 21 g |
| (2) Microcrystalline cellulose | 10 g |
| (3) Carboxymethylcellulose calcium | 7 g |
| (4) Light anhydrous silicic acid | 1 g |
| (5) Magnesium stearate | 1 g |
| (6) Dried extract of dried ginger obtained in Specific Example 3 | 160 g |
| total | 200 g |

The ingredients (1) to (6) were uniformly mixed and compression-moulded in a compression machine to give tablets (200 mg/tablet).

One tablet contains 160 mg of the dried extract of dried ginger obtained in Specific Example 3, and 20–80 tablets are administered daily into an adult at suitable intervals.

EXAMPLE 9

| | |
|---|---|
| (1) Corn starch | 188 g |
| (2) Magnesium stearate | 2 g |
| (3) Carboxymethylcellulose calcium | 8 g |
| (4) Light anhydrous silicic acid | 1 g |
| (5) Gingerol | 1 g |
| total | 200 g |

The ingredients (1) to (5) were uniformly mixed, compression-moulded in a compression machine, ground in a crusher and screened to give granules.

One gram of the granules contains 5 mg of gingerol and 1–10 g of the granules is administered daily into an adult at suitable intervals.

EXAMPLE 10

| | |
|---|---|
| (1) Corn starch | 19 g |
| (2) Light anhydrous silicic acid | 1 g |
| (3) Dried extract of dried ginger obtained in Specific Example 3 | 180 g |
| total | 200 g |

The ingredients (1) to (3) were uniformly mixed, and 200 mg was introduced into No. 2 capsule.

One capsule contains 180 mg of the dried extract of dried ginger, and 20–80 capsules are administered daily into an adult at suitable intervals.

EXAMPLE 11

300 g of alanine (pyrogen-free) was added to 20 L of a solution containing the extract of dried ginger obtained in Specific Example 4, and it was dissolved and lyophilized. The lyophilized sample was introduced into 900 vials to give an injection. This injection was of permeability sufficient to pass the pyrogen test in accordance with the Japanese Pharmacopoeia.

EXAMPLE 12

| | |
|---|---|
| (1) Dried extract of dried ginger obtained in Specific Example 3 | 0.05 g |
| (2) Isopropyl myristate | 5 g |
| (3) Plastibase | 94.95 g |

The ingredients (1) and (2) were mixed and added gradually to the ingredient (3) with stirring. The mixture was homogenized to give an oily ointment.

EXAMPLE 13

| | |
|---|---|
| (1) Gingerol | 0.05 g |
| (2) Isopropyl myristate | 5.95 g |
| (3) Isopropyl myristate | 10 g |
| (4) Vaseline | 66 g |
| (5) Liquid paraffin | 5 g |
| (6) Microcrystalline wax | 13 g |

The ingredients (3) to (6) were molten by heating, and a mixture (1) and (2) were added thereto at 45 to 50° C. It was homogenized under stirring until it was solidified to form an oily ointment.

EXAMPLE 14

| | |
|---|---|
| (1) Gingerol | 0.05 g |
| (2) Poly(ethyleneglycol) (400) | 11.95 g |
| (3) Poly(ethyleneglycol) (400) | 12 g |
| (4) Poly(ethyleneglycol) (4000) | 76 g |

The ingredients (3) and (4) were molten at 70° C., and a mixture of (1) and (2) was added thereto at 50° C. It was homogenized with stirring until it was solidified to form a hydrophilic ointment. Carbol 934™ can further be mixed with with the hydrophilic ointment.

INDUSTRIAL APPLICABILITY

The agent of the present invention has significant recovery effect of infection-protective ability, and it is useful to treat and prevent various infections such as virus infections, fungal infections and opportunistic infections.

I claim:

1. A method for treating a patient in need thereof viral infections comprising: employing a compound represented by the general formula (I):

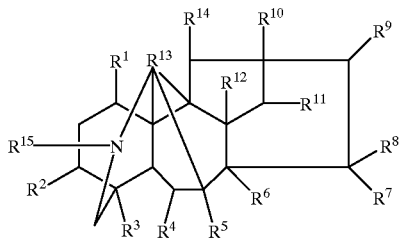

(I)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are the same or different and independently represent a hydrogen atom, hydroxyl group, substituted or unsubstituted $C_1$–$C_7$ alkyl group, substituted or unsubstituted $C_2$–$C_7$ alkenyl group, substituted or unsubstituted $C_2$–$C_7$ alkynyl group, substituted or unsubstituted $C_3$–$C_7$ cycloalkyl group, substituted or unsubstituted $C_4$–$C_7$ cycloalkenyl group, substituted or unsubstituted acyl group, substituted or unsubstituted acyloxy group, substituted or unsubstituted acyloxy-$C_1$–$C_7$ alkyl group, substituted or unsubstituted $C_2$–$C_7$ alkoxycarbonyl group, substituted or unsubstituted $C_2$–C7 alkenyl-oxycarbonyl group, substituted or unsubstituted aryloxycarbonyl group, substituted or unsubstituted $C_1$–$C_7$ alkoxy group, substituted or unsubstituted $C_2$–$C_7$ alkenyloxy group, substituted or unsubstituted $C_2$–$C_7$ alkynyloxy group, substituted or unsubstituted $C_3$–$C_7$ cycloalkyloxy group, substituted or unsubstituted $C_4$–$C_7$ cycloalkenyloxy group, substituted or unsubstituted aryloxy group, substituted or unsubstituted aryl-$C_1$–$C_7$ alkyloxy group, substituted or unsubstituted aryl-$C_2$–$C_7$ alkenyloxy group, substituted or unsubstituted $C_1$–$C_7$ alkoxy-$C_1$–$C_7$ alkyl group or substituted or unsubstituted $C_1$–$C_7$ alkoxy-$C_1$–$C_7$ alkoxy group, or $R^2$ and $R^3$ may together represent an epoxy group, $R^1$ and $R^{14}$ may together represent an epoxy group, and $R^7$ and $R^8$ may together represent an oxo group, or a pharmaceutically acceptable salt thereof.

2. A method according to claim 1, wherein the compound represented by the formula (I) is an aconite-alkaloid.

3. A method according to claim 1, wherein the viral infections are herpes infections.

4. A method according to claim 1, wherein the viral infections are acquired immunodeficiency syndromes.

5. A method according to claim 1, wherein the viral infections are cytomegalovirus infections.

6. A method according to claim 1, wherein the infections are opportunistic infections.

* * * * *